United States Patent [19]

Gorsuch et al.

[11] Patent Number: 5,152,743

[45] Date of Patent: Oct. 6, 1992

[54] APPARATUS AND METHOD FOR SELECTIVE SEPARATION OF BLOOD CHOLESTEROL

[75] Inventors: Reynolds G. F. Gorsuch, Yountville; John Atkin, Corona Del Mar, both of Calif.

[73] Assignee: Healthdyne, Inc., Marietta, Ga.

[21] Appl. No.: 570,029

[22] Filed: Aug. 20, 1990

Related U.S. Application Data

[63] Continuation-in-part of Ser. No. 229,007, Aug. 5, 1988, Pat. No. 4,950,224.

[51] Int. Cl.$^5$ ............................................. A61M 37/00
[52] U.S. Cl. ............................................. 604/4; 604/6
[58] Field of Search ........................................ 604/4-7, 604/48, 52, 53, 20, 29, 405, 406; 210/645, 646; 422/48

[56] References Cited

U.S. PATENT DOCUMENTS

| | | |
|---|---|---|
| Re. 31,688 | 9/1984 | Popovich . |
| 4,056,467 | 11/1977 | Christen et al. ............... 210/646 |
| 4,084,036 | 4/1978 | Leonard ............... 210/646 |
| 4,239,729 | 12/1980 | Hasagawa et al. ............... 422/48 |
| 4,240,907 | 12/1980 | Bentley . |
| 4,268,279 | 5/1981 | Shindo et al. ............... 422/48 |
| 4,276,173 | 6/1981 | Kell et al. ............... 210/646 |
| 4,389,363 | 6/1983 | Molthop . |
| 4,402,940 | 9/1983 | Nose et al. ............... 210/645 |
| 4,498,990 | 2/1985 | Shaldon . |
| 4,559,034 | 12/1985 | Kirita . |
| 4,563,170 | 1/1986 | Aigner . |
| 4,583,969 | 4/1986 | Mortensen . |
| 4,604,208 | 8/1986 | Chu . |
| 4,622,206 | 11/1986 | Torgeson ............... 422/48 |
| 4,623,327 | 11/1986 | Mahurkar . |
| 4,631,053 | 12/1986 | Taheri . |
| 4,767,400 | 8/1988 | Miller . |
| 4,769,037 | 9/1988 | Midcalf . |
| 4,776,837 | 10/1988 | Kopp ............... 604/4 |
| 4,790,331 | 12/1988 | Okada . |
| 4,808,315 | 2/1989 | Manabe et al. ............... 210/645 |
| 4,820,261 | 4/1989 | Schmoll . |
| 4,850,958 | 7/1989 | Berry . |
| 4,854,322 | 8/1989 | Ash et al. ............... 604/48 |
| 4,874,522 | 10/1989 | Okamoto et al. ............... 210/645 |
| 4,923,679 | 5/1990 | Fukasawa et al. . |
| 4,968,432 | 11/1990 | Antwiler ............... 604/5 |

FOREIGN PATENT DOCUMENTS

2606642 5/1988 France .
2616666 12/1988 France .

Primary Examiner—Randall L. Green
Assistant Examiner—R. Clarke
Attorney, Agent, or Firm—Jones, Askew & Lunsford

[57] ABSTRACT

Selective separation of blood cholesterol by cascade filtration. An in vivo filter is implanted within a blood vessel to separate plasma from blood, and the separated plasma is removed to an extracorporeal secondary filter which removes low density lipoprotein (LDL) from the plasma. The in vivo portion of the apparatus comprises a number of microporous hollow fibers sized to permit diffusion of plasma, but not cellular or other larger blood components, through the fiber pores to the hollow interior of the fibers. The secondary filter passes the removed plasma along membrane walls formed by fibers sized to block passage of LDL while permitting passage of other plasma components, so that approximately 95 percent of LDL is separated from the plasma before the plasma is returned to the body in real time after removing the LDL cholesterol.

11 Claims, 3 Drawing Sheets

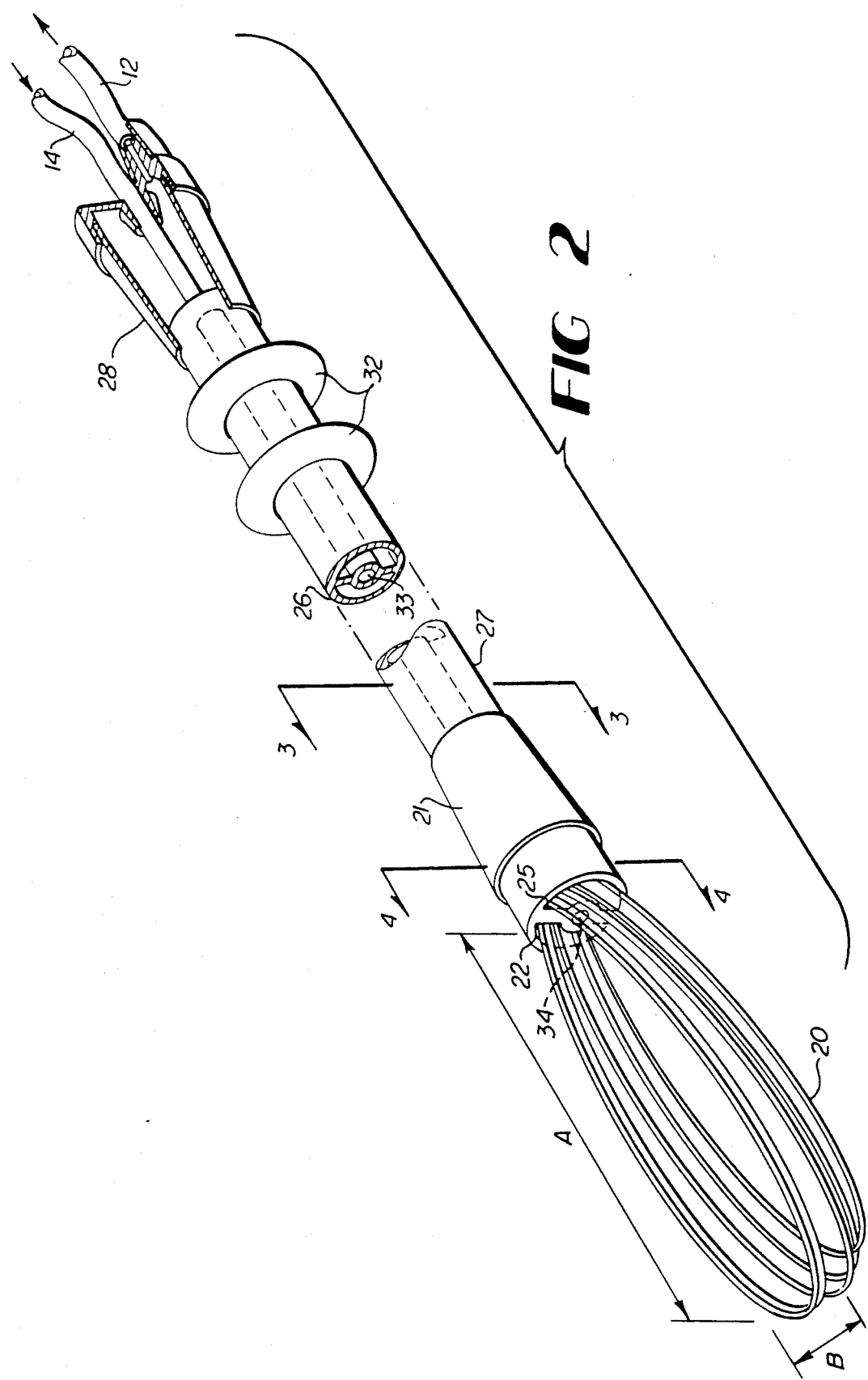

APPARATUS AND METHOD FOR SELECTIVE SEPARATION OF BLOOD CHOLESTEROL

CROSS-REFERENCE TO RELATED CASE

This is a continuation-in-part of Ser. No. 07/229,007 filed Aug. 5, 1988, U.S. Pat. No. 4,950,224.

FIELD OF INVENTION

This invention relates in general to the reduction of blood cholesterol, and relates in particular to the reduction of low density lipoprotein cholesterol by cascade filtration of whole blood.

BACKGROUND OF THE INVENTION

The single largest health problem in the United States today is heart and vascular disease. A large portion of that problem is atherosclerosis of the coronary and peripheral arteries. Hundreds of thousands of patients each year undergo balloon angioplasty or open heart surgery for coronary bypass procedures. Current clinical studies show that angioplasty patients are at risk for repeat angioplasty, or progression to bypass procedures at the rate of 30% or higher. Numerous epidemiological studies have linked high plasma cholesterol levels with the amount of atherosclerotic plaque. Other studies have shown that a reduction of risk can be achieved with a reduction of plasma cholesterol. Further studies have shown that atherosclerotic plaque can be abated or removed under conditions of very low cholesterol levels (around 150 mg/dl) coupled with a low ratio of low-density lipoprotein (LDL) cholesterol to high density lipoprotein (HDL) cholesterol.

A coronary primary prevention trial published by the Lipid Research Center under funding by the National Institute of Health (1984) showed that lowering cholesterol levels in individual patients reduces the risk of heart attack, angina, abnormal stress tests, need for coronary bypass, and cardiac death. This trial showed that for every 1% reduction of cholesterol, there was a 2% reduction in the above cardiovascular complications. The trial further showed that for patients on a low-cholesterol diet and medicated with cholestryamine, total cholesterol levels were reduced by 13%, LDL was reduced by 20%, and there was a statistically significant 24% reduction in nonfatal heart attacks or coronary heart disease-related deaths, relative to the control group.

Most of the cholesterol in the human body is manufactured in the liver. Some of this cholesterol is turned into bile which is excreted by the liver via the bile ducts into the small intestine. While in the intestine, the bile aids in digestion and is then reabsorbed in the ileum. The bile there is broken down and turned back into cholesterol. The level of cholesterol in circulation in the blood depends in large part on the rate of clearance of LDL from circulation by the liver. The clearance rate of the liver, in turn, depends on the number of LDL receptors on the surface of the liver cells. It turns out that the number of LDL receptors is under feedback regulation according to the amount of cholesterol in the liver. If there is a lot of cholesterol in the liver, receptor synthesis goes down, less LDL is cleared from circulation, and serum cholesterol remains dangerously high. If there is not that much cholesterol in the liver, LDL is cleared more effectively and cholesterol levels stay down.

Cholesterol in the bloodstream, known as serum cholesterol, circulates bound to two special proteins, low density lipoprotein (LDL) and high density lipoprotein (HDL). Two other lipoproteins, the chylomicrons and the very low density lipoproteins, are relatively unimportant although both ultimately convert to LDL. LDL is "bad cholesterol" and high levels are associated with atherosclerosis. HDL, on the other hand, is "good cholesterol" and is seen as something of a scavenger to remove errant cholesterol from the system. Because most cholesterol is bound to LDL, total serum cholesterol parallels the LDL levels in the bloodstream.

Hypercholesteromia is considered to exist for cholesterol levels above 240 mg/dl and ranges from that level up to 1000 mg/dl. A large portion of patients have cholesterol levels in the 300–500 mg/dl level. There are several current methods of treatment for patients with hypercholesterolemia. The efficacy of drug therapy for reduction of coronary risk in hypercholesterolemic patients has been demonstrated through the use of effective drugs such as reductase inhibitors. However, many researchers have reservations about the broad use of drugs for treatment of hypercholesterolemia. Almost all drugs have side effects or the potential for side effects. Adverse reactions sometimes do not become manifest for many years and only after large numbers of patients have been treated. Furthermore, a positive benefit/risk ratio for cholesterol-lowering drugs will be difficult to prove, as the cost in terms of expensive drugs, laboratory monitoring for response and side effects, and physician involvement must be balanced against the benefits to be achieved.

Moderate reduction in cholesterol levels can be achieved in most patients with dietary modification alone. Some patients will show a dramatic response to a dietary change. Although dietary modification overall may not be as potent as drugs for cholesterol lowering, modification of the diet reduces the cost of medication and avoids the problem of side effects. A significant portion of patients can obtain a satisfactory response to dietary change, and drugs thus are difficult to justify, particularly for those who have become hypercholesterolemic because of dietary excesses.

In many patients, drugs and diet cannot reduce cholesterol levels more than 25 to 30 percent. For those patients, therapeutic plasmapheresis has been proposed for the treatment of hypercholesterolemia. The term "plasmapheresis" is commonly defined as the removal of whole blood from the body, separation of the plasma from the removed whole blood, treatment of the plasma to remove a component such as cholesterol, and then reinfusing the treated plasma into the patient. Typical plasmapheresis techniques can cause damage to the blood cells during separation from the plasma, which is commonly done by centrifugation. Investigations have shown that by weekly plasmapheresis procedures, patients with severe hypercholesterolemia can be maintained at an average level of 120–150 mg/dl with cyclic swings between 70 and 190 mg/dl. These patients appear to regenerate cholesterol at the rate of 100 mg/dl/week. These procedures involve weekly trips to the hospital with two liters of blood removed and replaced in a process similar to kidney hemodialysis procedure, with the attendant trauma to the blood, the cardiovascular system, and patient well-being. Moreover, extracorporeal separation of blood cells increases the possibility of infection or contamination from the mechanical apparatus, technician error, environmental conditions, or other sources. In general, therapeutic plasmapheresis is considered an extreme method for treatment of hypercholesterolemia, and would only be considered after a complete regime of both diet and drugs had been ineffective in lowering cholesterol levels.

SUMMARY OF THE INVENTION

Stated in general terms, the present invention accomplishes removal of cholesterol from the bloodstream by separating plasma from the blood in vivo and then treating the plasma extracorporeally to remove a selected component of cholesterol from the plasma. The treated plasma is returned to the bloodstream in real time. The returned plasma includes protein, albumen, and other autologous plasma components. Real-time operation permits adjusting the throughput rate of the plasma to a continuous atraumatic level which avoids the shock and trauma of batch blood treatment procedures. Real-time processing also permits downsizing the apparatus to be portable and relatively ambulatory, thus providing a therapeutic process which is socially acceptable and amenable to an active, productive lifestyle. Moreover, such treatment according to the present invention is highly cost effective when compared to the alternatives of secondary angioplasty or bypass surgery.

Stated in somewhat greater detail, in vivo separation of plasma from other blood components is accomplished through a membrane implantable in a blood vessel, such as the vena cava, and functioning as a filter to admit plasma while preventing other blood components from passing through the membrane. The plasma separated by the membrane then is removed from the body and cholesterol preferably is separated from the removed plasma by secondary filtration, a procedure which offers several advantages over procedures involving plasma exchange. These advantages include no requirement for exogenous protein replacement, avoidance of side effects and reactions sometimes encountered with commercial albumen replacement solutions used for volume repletion, and the danger of transmitting viral diseases such as hepatitis, AIDS, or cytomegalovirus.

Stated somewhat more specifically, in vivo separation of plasma is accomplished by apparatus comprising at least one and preferably a plurality of microporous hollow fibers implantable in a blood vessel and having a pore size sufficient to admit plasma while preventing other blood components from entering the hollow interior of the fiber. These fibers can be made of polypropylene or other appropriate material. The separated plasma is transported to the exit lumen of a catheter which conducts the plasma to an extracorporeal filter comprising a membrane of material having a pore size sufficient to allow the LDL in the plasma to diffuse through the pores but not sufficient to allow plasma components larger than LDL to diffuse therethrough in significant amount.

The extracorporeal filter in one preferred embodiment is a multiple-pass filter which is used for long-term continuous application of the present method. This filter recirculates the withdrawn plasma over the filter membrane to optimize and regulate recovery of essential plasma constituents. An alternative preferred embodiment of the extracorporeal filter in the present invention utilizes a single-pass dead end filter membrane for short term procedures, where optimum performance is not necessary and where maximum recovery of protein and other constituents is not vital. A suitable pump returns the treated plasma from the extracorporeal filter to the bloodstream by way of a return lumen through the catheter.

Accordingly, it is an object of the present invention to provide an improved apparatus for reduction of blood cholesterol.

It is another object of the present invention to provide an apparatus for reduction of blood cholesterol wherein plasma is separated from blood in vivo and cholesterol is extracorporeally removed from the separated plasma.

It is a further object of the present invention to provide selective separation of cholesterol from the bloodstream by cascade filtration including in vivo separation of plasma from cellular components of blood and extracorporeal removal of cholesterol from the separated plasma.

It is still another object of the present invention to provide an apparatus and method for reducing blood cholesterol by removing low density lipoproteins from the blood at a continuous throughput rate which avoids the shock and trauma of batch procedures, and which does not require exogenous protein replacement.

Other objects and advantages of the present invention will become more readily apparent from the following description of preferred embodiments.

BRIEF DESCRIPTION OF DRAWINGS

FIG. 2 is an enlarged pictorial view, partially broken away for illustrative purposes, showing the in vivo plasma separation apparatus.

DETAILED DESCRIPTION OF PREFERRED EMBODIMENTS

Figure 1:
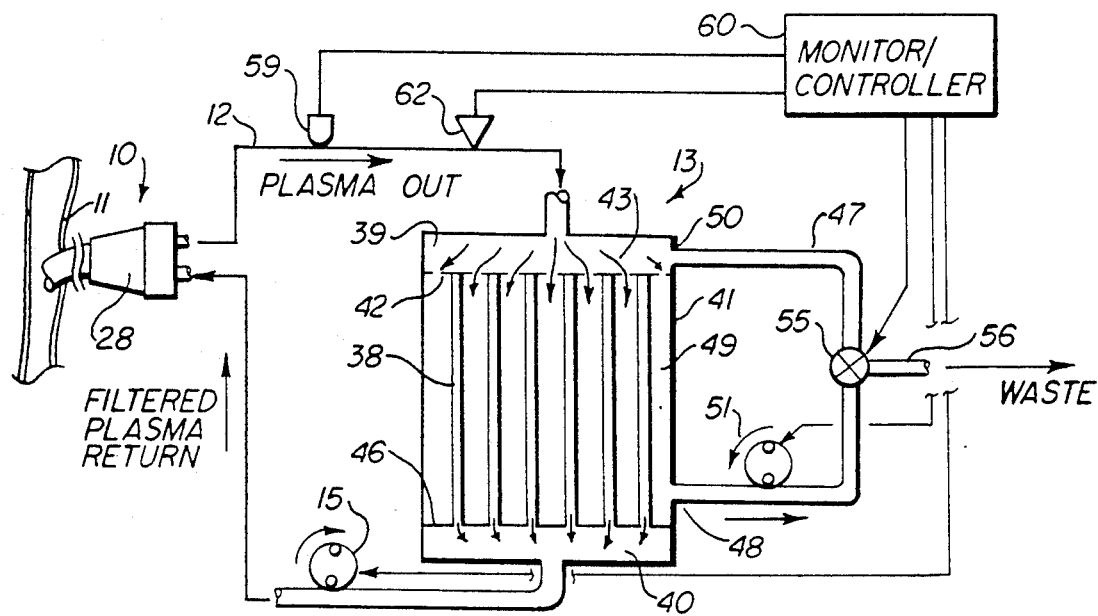
FIG. 1 is a partially schematic view showing a preferred embodiment of the present invention including an apparatus for in vivo separation of plasma and a first embodiment of a secondary filter for separation of LDL from plasma.

Turning first to FIG. 1 for an overview of the invention, 10 generally denotes a plasma separation apparatus shown inserted in a vein 11 of a patient undergoing selective separation of blood cholesterol. The plasma separation apparatus 10 functions as a primary filter to separate plasma from the cellular products of blood flowing through the vein 11, and the separated plasma leaves the patient through the plasma exit tube 12 connected to the plasma separation apparatus 11. The plasma exit tube 12 conducts the separated plasma to the cholesterol removal filter 13 where LDL is separated from the plasma in a manner described below in greater detail. A plasma return tube 14 connects to the plasma outlet of the cholesterol removal filter 13 and conducts the treated plasma back to the plasma separation apparatus 10, where the treated plasma is reintroduced to the patient's bloodstream within the vein 11. A pump 15, preferably a peristaltic pump or the like, provides positive displacement of the treated plasma within the plasma return tube 14. It will thus be appreciated that the plasma separation apparatus 10 functions as an in vivo primary filter to separate plasma from the blood, and that the cholesterol removal filter 13 functions as a secondary filter in cascade with the primary filter for removal of LDL from the separated plasma.

Details of the plasma separation apparatus 10 are shown in FIG. 2. The in vivo plasma separator apparatus 10 comprises at least one and preferably a plurality of hollow microporous fibers 20 each having a hollow interior disposed longitudinally therein. The fibers 20 can be made of any suitable material such as polymeric plastic, but are preferably polymeric polypropylene. The fibers 20 can be made by methods known to those skilled in the art. For example, polypropylene can be mixed with a solvent and the mixture spun; as the solvent and polymer phase are separated the fiber is formed. One suitable fiber commercially available is Plasmaphan ® membranes made from polypropylene polymer (ENKA AG, Wuppertal, West Germany). The fibers 20 possess a microporous structure having a very high void volume, low variation in pore distribution, and high reproducibility in production. The fiber pore size is sufficient to admit plasma to pass through the wall of the hollow fiber and into the hollow center of the fiber, although the overall size of the fibers should not significantly obstruct fluid flow through the blood vessel. Cellular components of the blood, however, are unable to diffuse through the fiber pores. Predominantly large molecules will pass around the apparatus 10 within the vein fluid flow. The vein fluid flow also prevents clogging of the pores. The fiber pore size can be from about 0.1 to 1.0 $\mu$m; preferably, from about 0.2 to 0.8 $\mu$m; and more preferably, from about 0.4 to 0.6 $\mu$m.

The fibers 20 are longitudinally aligned in a generally parallel or radial orientation. The plurality of fibers 20 provide a large available surface area through which plasma can diffuse. The individual fibers can be arranged in a bundle to ensure adequate fluid-membrane contact along substantially the entire exterior surface of the membrane. The fibers 20 preferably are loosely bundled so as to improve surface area contact with blood.

Figure 4:
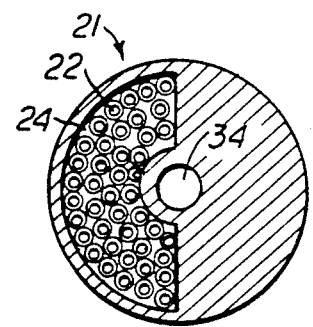

The fibers 20 constitute the active element of the plasma separation apparatus 10. Each individual fiber 20 defines a generally elongated loop extending outwardly from the distal header 21 to which the fibers are connected. The fibers 20 are connected to the distal header 21 by standard potting and cutoff techniques used in the medical industry in the manufacture of hollow fiber oxygenators and hollow fiber kidney dialysis membrane filters, for example. In this process, the fibers are potted into a solid block of plastic or epoxy, fixing their position, and the block then is cut transverse to the fibers to expose their open ends to a chamber for gas or fluid access. The connected fibers 20 describe a generally circular pattern at the distal header 21, as seen in FIG. 2. However, in the disclosed embodiment only one end 22 of each fiber 20 remains open to fluid flow communication with the manifold chamber 24 within the distal header 21, as shown in FIG. 4. That manifold chamber 24 occupies approximately half the circular arc of the distal header 21, and in turn is in fluid flow communication with an outer lumen 26 of the triple-lumen catheter 27 connected between the distal header 21 and the proximal header 28, FIG. 2. Each fiber 20 thus describes a loop commencing at one end 22 open to the manifold chamber 24 within the distal header 21, and terminating at the other end 25 which is closed within the potted distal header. The full length of the hollow interior in each fiber 20 thus is in fluid communication with the outer lumen 26 of the catheter 27.

Figure 5:
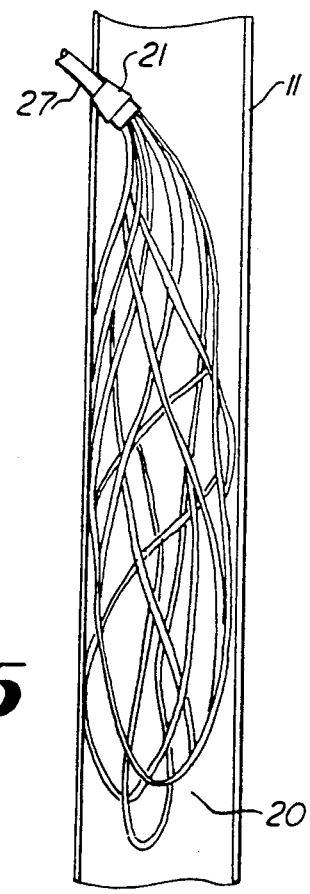
FIG. 5 is a section view of the apparatus shown in FIG. 2 when implanted in a blood vessel.

The portion of the plasma separation apparatus 10 inserted into the vein 11 includes the active elements made up of the fibers 20 and the distal header 21, as illustrated in FIG. 5. The techniques for placing the plasma separation apparatus 10 in a suitable vein are described in detail in U.S. Pat. No. 4,950,224, which is incorporated herein by reference. The catheter 27 extends outwardly from the distal header 21 to the proximal header 28, from which the plasma exit tube 12 and the plasma return tube 14 connect the plasma separation apparatus 10 to the cholesterol removal filter 13 as shown in FIG. 1. A pair of anti-bacteria barriers 32 are located surrounding the catheter 27 adjacent the proximal header 28 to prevent infection near the exit of the catheter from the skin. The ringlike barriers 32, which can be greater or fewer in number than two, are made of a nonreactive porous material having a relative uniform pore size sufficient to prevent bacteria from passing through the barriers yet permitting smaller molecules to pass therethrough. The porous nature of the barriers 32 also promotes ingrowth of body tissue for anchoring the implanted catheter 27 within the body.

Figure 3:
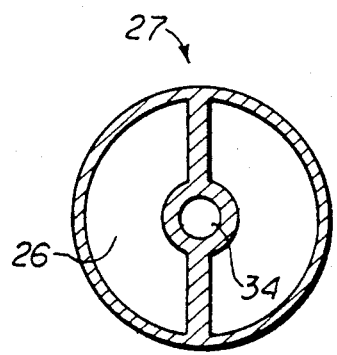
FIGS. 3 and 4 are section views taken respectively along lines 3—3 and 4—4 of FIG. 1.

The catheter 27, as mentioned previously, is a triple-lumen catheter having an axial center lumen 33 surrounded by a pair of outer lumens. One outer lumen 26 is connected to the manifold chamber 24 in communication with the open ends 22 of the fibers 20; the other outer lumen of the triple-lumen catheter is not used in the disclosed embodiment. The center lumen 33 is connected at the proximal header 28 to the plasma return tube 14, and extends through the distal header 21 to the plasma return outlet 34 (FIGS. 2 and 3) located between the open ends 22 and closed ends 25 of the fibers 20.

Plasma transfer through the fibers 20 is accomplished within the vein 11 as blood flowing through the vein comes in contact with the porous fibers. Plasma fluid and dissolved molecules are sufficiently small to diffuse through the membrane of the fibers 20 and into the hollow center of each fiber. Diffusion can occur passively, although preferably by means of the external negative pressure applied within the hollow center of the fibers by means of the pump 15 (FIG. 1) operating on the plasma return tube 14.

The number and length of fibers 20 for use with the plasma separation apparatus 10 depends on the needs of the particular patient. In general, patients will vary with initial plasma cholesterol levels between 300 mg/dl to over 1000 mg/dl. Consequently, plasma separation apparatus having at least two plasma-separation capacities will be required to handle the lower and higher levels of cholesterol concentration, respectively. For the lower level of cholesterol concentration, plasma flows of 2 to 3 ml/min are required, and for the upper levels of concentration, plasma flows of 6 to 8 ml/min may be required. These rates of plasma separation and flow require a range of 30 to 120 $cm^2$ surface area of the plasma separation fibers 20 to meet the flow requirements. Referring to FIG. 2 where A denotes the length of each individual loop of fiber 20 when elongated so that the two sides of the loop are substantially parallel with each other, and where B denotes the overall diameter of the bundle of fibers as thus elongated, the following table shows two configurations of the plasma extraction fibers meeting those two requirements:

|   | 120 cm² | 30 cm² |
| --- | --- | --- |
| A | 2.68" | 2" |
| B | 0.18" | 0.09" |
| No. of fibers | 50 | 25 |

It should be evident that other configurations of fibers may be provided which meet the overall surface area requirements mentioned herein, and that other surface areas may be appropriate for the needs of other patients.

Returning to FIG. 1, the cholesterol removal filter 13 removes LDL from the separated plasma by filtering the plasma through a plurality of fibers 38 extending within the closed housing 41 between the inlet or proximal header 39 and the outlet or distal header 40. The upper ends of the hollow fibers 38, as viewed in FIG. 1, are closed at the perforated wall 42 separating the proximal header 39 from the remainder of the interior within the housing 41. The perforations in the header wall 42 allow the plasma to enter the interior 49 of the housing 41 to flow through the wall and around the outsides of the hollow fibers 38, as indicated by the arrows 43.

The lower ends of the hollow fibers 38 extend through the imperforate distal header wall 46 which separates the distal header 40 from the remainder of the housing 41. The plasma return tube 14 connects to the outlet header 40 by way of the pump 15 for withdrawing filtered plasma from the outlet header.

The cholesterol removal filter 13 includes a recirculation loop 47 having an inlet end 48 communicating with the interior 49 of the housing 41, and having an outlet 50 communicating with the inlet header 39. The inlet 48 of the recirculation loop is located between the proximal wall 42 and the distal wall 46, preferably at a location adjacent the distal wall. A pump 51, which also may be a peristaltic pump, engages the tubing forming the recirculation loop 47 so as to draw fluid into the recirculation loop from the interior 49 at the inlet 48, and to return that withdrawn fluid to the proximal header 39 through the outlet 50.

A diversion valve 55 is located in the recirculation loop 47 preferably downstream from the pump 51. This valve 55 normally operates to pass the pumped fluid through the valve for return to the proximal header 39. However, the valve 55 is selectively actuatable for diverting the pumped fluid to the waste line 56 which extends to a waste bag (not shown) or other receptacle for receiving the waste cholesterol from the system.

A pressure transducer 59 is operatively in line with the exit tube 12 conducting plasma from the plasma separation apparatus 10 to the LDL separation module 13. The pressure transducer 59 measures the pressure of the plasma in the exit tube 12 for providing a safety parameter to determine proper functioning of the system, and for providing an input to the monitor/controller 60 which preferably controls operation of the plasma return pump 15 and the pump 51 in the recirculation loop 47. Also in line with the plasma exit tube 12 is the cholesterol sensor 62 which measures cholesterol levels in the plasma for the purpose of noting patient response to the cholesterol removal operation, and for control purposes in regulating total flow rate through the exit tube 12. The cholesterol sensor 62 preferably is of the optical turbidity type; that sensor as well as an appropriate pressure sensor 59 are known in the art.

The described cholesterol separation system operates as follows. Plasma from the in vivo separation filter 10 passes through the exit tube 12 and enters the proximal header 39 of the cholesterol removal filter, where the plasma passes through the perforate upper wall 42 and enters the interior 49 of the housing 41 to flow along the outsides of the hollow filter fibers 38. The pore size of these fibers is selected so that approximately 50% of the proteins, albumin, and other components of the plasma, but not of the LDL cholesterol, pass through the fiber membrane and into the hollow interior of the fibers. However, only approximately 5% of the LDL in the plasma enters the hollow fibers 38. The exudate or filtered return plasma thus is obtained from the hollow interior of each fiber 38 and flows to the distal outlet header 40, where the filtered plasma is returned via the plasma return tube 14 and the pump 15 to the in vivo apparatus 10. The filtered plasma passes through the catheter 27 to the distal header 21 along the center lumen 33, where the returned plasma exits the plasma outlet opening 34 to re-enter the bloodstream in the vein 11.

The remaining 50% of the plasma which originally entered the inlet header 39, plus the 95% of the LDL which did not pass through the fibers 38 and thus remained in the interior 49 of the housing 41, is removed at the lower or distal end of the housing 41 and returned to the proximal header 39 by way of the recirculation loop 47. The recirculated liquid there recirculates over the LDL-removal filter formed by the fibers 38, thus allowing more proteins and other non-LDL components of the recirculate to diffuse into the hollow interiors of the fibers 38 and passing into the fibers only 5% of the LDL in the recirculate. The pump 51 in the recirculation loop 47 is operated at a rate to provide a flow velocity through the recirculation loop which is several times the inlet/outlet velocity of plasma flowing from the body through the tubes 12 and 14. Thus, it is apparent that the concentration of LDL in the recirculation loop 47 will build up to a point where the filter functioning of the fibers 38 will lose efficiency. When that occurs, the diversion valve 55 is opened and the entire LDL-rich contents of the recirculation loop is discharged to waste, thus removing the waste cholesterol from the system.

The monitor/controller 60 monitors the plasma pressure input from the sensor 59 and the cholesterol level input from the sensor 62, and provides command control signals to the plasma return pump 15 and the recirculation loop pump 51 according to physician-determined values of those parameters. The monitor/controller 60 preferably also controls operation of the diversion valve 55, which can remove waste cholesterol from the system either on the basis of timed operation in view of the flow rates selected by the pumps, or on cholesterol level input to the system as measured by the cholesterol sensor 62, or otherwise as determined by the system operator. Alternatively, the pump 15 and the rest of the apparatus can be manually operated.

Figure 6:
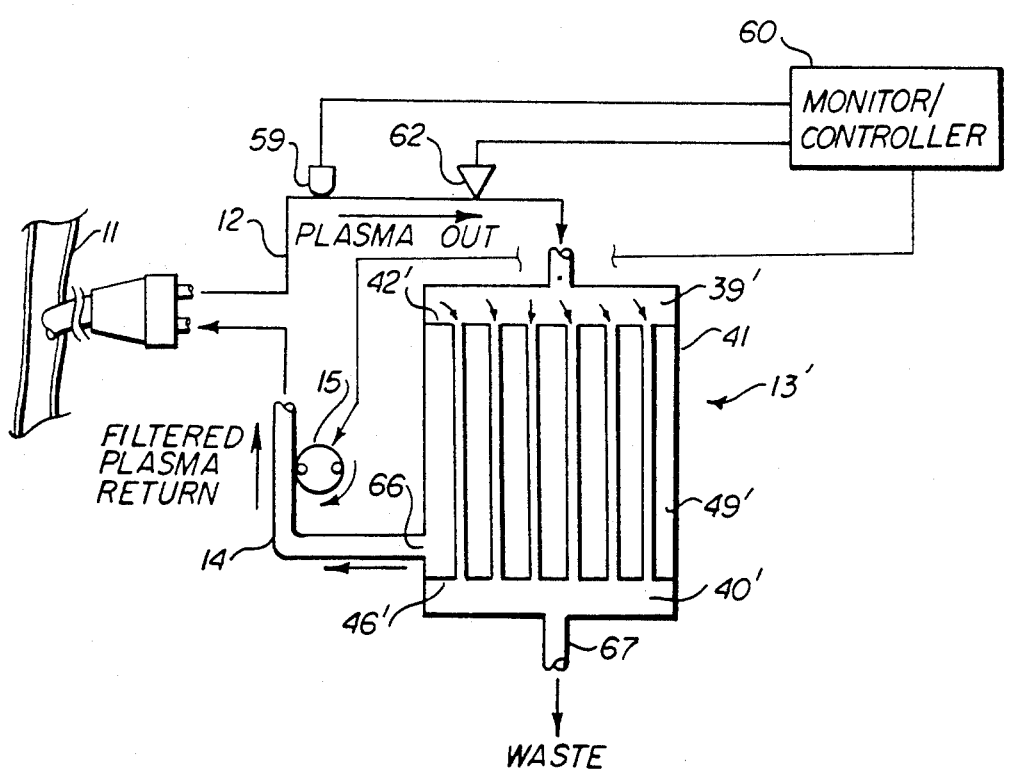
FIG. 6 is a partially schematic view showing another embodiment of the present invention including the plasma separation apparatus shown in FIG. 2 and a second embodiment of LDL separation filter.

The embodiment shown in FIG. 6 utilizes a single-pass cholesterol removal filter 13' instead of the recirculating filter 13 shown in FIG. 1. Plasma removed from the body by the in vivo apparatus 10 flows once through the filter 13' and is returned to the body through the return tube 14 by means of the pump 15. Within the housing 41 of the filter 13' are a number of filter fibers 38' whose porous construction, like that of the fibers 38, substantially prevents entry of LDL cholesterol but permits relatively significant entry of HDL cholesterol, protein, albumen, and other components of the plasma. The hollow interior of each fiber 38' is open at the proximal wall 42', allowing the incoming plasma to flow into the fibers. The hollow interior of each fiber 38 also is open to the distal wall 46' separating the distal header 40' from the interior 49' of the housing 41. However, the filtered plasma is withdrawn not from the distal header 40, but from an outlet 66 communicating with the interior 49' near the distal wall 46'. Thus, plasma from the patient enters the distal header 39' and flows into the hollow interiors of the fibers 38', but the exudate through the fibers is returned from the interior chamber 49' surrounding the outer surface of the fibers. Because the pore size of the fibers 38' blocks substantially all LDL cholesterol while permitting significant passage of other plasma components, the majority of protein and other non-LDL components passes through the walls of the fibers 38' and is pumped through the outlet 66 for return to the body, while about 95 percent of the LDL remains within the hollow interiors of the fibers. This retained LDL flows into the distal header 40' and exits the filter 13' through the waste outlet 67.

The length of the fibers 38' in the non-recirculating filter 13' should be suitably sized to the flow rate of the input plasma such that the majority of non-LDL components are recovered as exudate through the fibers and about 95 percent of the LDL is removed. Alternatively, several filters 13' could be placed in series where the outlet 66 of a first such filter would become the inlet of a second such filter, and so on to provide the aggregate length of fibers 38' necessary for the desired removal of LDL at the desired flow rate of plasma through the filters.

Filter fibers 38 and 38' of various commercial standard or custom hollow fibers may be used for the cholesterol removal filters according to the present invention. A custom fiber may be constructed to provide the appropriate pore size of about 0.003 to 0.01 $\mu$m, preferably from about 0.003 to 0.007 $\mu$m, and more preferably from about 0.003 to 0.004 $\mu$m. Alternatively, the fibers 38 or 38' may be provided using Enka PF100 fiber made of cellulous-2.5-acetate polymer having an inner diameter of approximately 350 $\mu$m and a wall thickness of about 85 $\mu$m. A filter designed to remove only LDL cholesterol at a nominal 3 ml/min of plasma flow and operating with a trans-membrane differential pressure of 75 mm Hg would need 300 cm$^2$ of surface area. For this requirement, the filter module would be 3 inches long and 0.4 in diameter, having 200 fibers of 450-micron diameter with a packing density of 50 percent in a U-shaped configuration. Those skilled in the art will realize that other physical arrangements may be substituted so long as the filter requirements for the selected flow rate of plasma from the body are met. The filters for the modules 13 and 13' preferably are in cartridge form for case of replacement when necessary.

The present system including the in vivo plasma separation filter could be used for procedures involving separation of LDL by plasma exchange instead of cascade filtration. However, cascade filtration as disclosed herein offers several advantages. For one, there is no requirement for exogenous protein replacement. Commercial albumen solutions used for volume repletion have side effect reactions in about 20 percent of treatment. Only expensive high-quality albumen preparations at a low rate of side reactions in the order of one percent. Fresh frozen plasma is not a practical alternative for volume repletion because of an even higher rate of immediate side reactions compared to commercial albumen solutions.

It should also be understood that the foregoing relates only to preferred embodiments of the present invention, and that numerous modifications and changes therein may be made without departing from the spirit and scope of the invention as defined in the following claims.

We claim:

1. An apparatus using in vivo separation of plasma from blood for selective separation of blood cholesterol, comprising:

at least one elongated microporous fiber having a hollow interior, said fiber being dimensioned to be received within a blood vessel without significantly obstructing fluid flow through said blood vessel, the pore size of the fiber being sufficient to allow plasma to diffuse through the pores into the hollow interior of the fiber but not sufficient to allow cellular components larger than plasma to diffuse therethrough;

the hollow interior of said elongated fiber being in fluid communication with a means for conducting plasma comprising a first hollow tube which connects to the hollow interior of the fiber and permits passage of plasma from the fiber, and a second hollow tube which returns plasma to said blood vessel;

extracorporeal filter means receiving the plasma passing through the first tube and removing low density lipoproteins from the plasma; and means conducting the plasma from the extracorporeal filter means to the second hollow tube for return to the blood vessel.

2. Apparatus as in claim 1, wherein the last-mentioned means comprises a pump for moving the plasma from the extracorporeal filter means to the second hollow tube.

3. Apparatus as in claim 1, wherein the fiber is composed of a polymeric material having a pore size of from about 0.1 to 1.0 $\mu$m.

4. Apparatus as in claim 1, wherein the fiber is composed of a polymeric material having a pore size of about 0.2 to 0.8 $\mu$m.

5. Apparatus as in claim 1, wherein the fiber is composed of a polymeric material having a pore size of about 0.4 to 0.6 $\mu$m.

6. Apparatus as in claim 1, wherein the extracorporeal filter means comprises at least one hollow fiber of polymeric material having pore size sufficient to allow the low density lipoprotein in the plasma to diffuse through the pores but not sufficient to allow plasma components larger than low density lipoprotein to diffuse therethrough.

7. Apparatus as in claim 4, wherein the fiber of the extracorporeal filter means has a pore size of about 0.003 to 0.004 $\mu$m.

8. An apparatus using in vivo separation of plasma from blood for separation of blood cholesterol, comprising:

at least one elongated microporous fiber having a hollow interior and dimensioned to fit within a blood vessel;

the pore size of the fiber being sufficient to allow plasma to diffuse through the pores into the hollow interior but not sufficient to allow cellular components larger than plasma to diffuse therethrough;

a header connected in fluid flow communication with the interior of the fiber;

a first hollow tube connected to the header to receive the plasma from the interior of the fiber;

extracorporeal means receiving the plasma passing through the first tube and operative to remove low density lipoprotein from the plasma;

a second hollow tube connected to the header and receiving the plasma from the extracorporeal means; and a pump operative to return the plasma, after the removal of low density lipoprotein therefrom, through the second hollow tube to the header for return to the blood vessel.

9. The apparatus as in claim 8, wherein the microporous fiber has a pore size of about 0.1 to 1.0 μm.

10. A method using in vivo separation of plasma from blood for selective separation of blood cholesterol, comprising the steps of:

implanting in a blood vessel at least one elongated microporous fiber having a hollow interior and dimensioned for placement within a blood vessel without significantly obstructing fluid flow through the blood vessel, the pore size of the elongated microporous fiber being sufficient to allow plasma to diffuse through the pores into the hollow interior of the fiber but not sufficient to allow cellular components larger than plasma to diffuse therethrough;

placing the hollow interior of said elongated fiber in fluid communication with a first hollow tube which permits passage of plasma from the fiber;

removing plasma from the blood vessel through the first hollow tube;

treating the removed plasma to remove low-density lipoprotein from the plasma; and then re-infusing the plasma into the blood vessel.

11. A method for selective removal of blood cholesterol from a patient, comprising the steps of:

separating plasma in vivo within a blood vessel of the patient from cellular components larger than plasma of blood therein;

removing the separated plasma from the blood vessel and extracorporeally treating the removed plasma to remove low density lipoprotein from the plasma; and then reinfusing the plasma into the blood vessel.

* * * * *